(12) United States Patent
Glickman et al.

(10) Patent No.: US 7,671,078 B2
(45) Date of Patent: Mar. 2, 2010

(54) ISOTHIOUREA DERIVATIVES OF IMADAZO[2,1-B]THIAZOLES AND 5,6-DIHYDRO DERIVATIVES THEREOF USEFUL AS CXCR4 CHEMOKINE RECEPTOR INHIBITORS

(75) Inventors: Fraser Glickman, Basel (CH); Markus Streiff, Birsfelden (CH); Gebhard Thoma, Lörrach (DE); Hans-Günter Zerwes, Lörrach (DE)

(73) Assignee: Novartis AG, Basel (CH)

( * ) Notice: Subject to any disclaimer, the term of this patent is extended or adjusted under 35 U.S.C. 154(b) by 334 days.

(21) Appl. No.: 10/590,399

(22) PCT Filed: Feb. 25, 2005

(86) PCT No.: PCT/EP2005/002014
§ 371 (c)(1),
(2), (4) Date: Sep. 26, 2006

(87) PCT Pub. No.: WO2005/085219
PCT Pub. Date: Sep. 15, 2005

(65) Prior Publication Data
US 2007/0161618 A1    Jul. 12, 2007

(30) Foreign Application Priority Data
Feb. 27, 2004    (GB) .................. 0404434.3

(51) Int. Cl.
C07D 513/04 (2006.01)
A61K 31/429 (2006.01)
C07D 513/14 (2006.01)
A61K 31/519 (2006.01)
A61P 35/04 (2006.01)
A61P 37/06 (2006.01)
A61P 31/14 (2006.01)

(52) U.S. Cl. .................. 514/368; 514/63; 514/64; 514/260.1; 514/366; 548/110; 548/147; 548/151; 544/229; 544/278; 544/230

(58) Field of Classification Search .............. 548/110, 548/147, 154; 514/63, 64, 368
See application file for complete search history.

(56) References Cited

U.S. PATENT DOCUMENTS 3,542,802 A    11/1970    Tweit
3,881,015 A    4/1975    Black et al.
4,041,167 A    8/1977    Moser et al.
4,098,898 A    7/1978    Durant et al.
4,293,549 A    10/1981    Rachlin et al.
4,556,669 A    12/1985    Nishio et al.
4,736,038 A    4/1988    Yamamoto et al.

OTHER PUBLICATIONS

Daniel Zahari et al., "L'Obtention Et L'Evaluation De L'Activite Antimicrobienne De Quelques 2-Ary-5-R-Thiazolo[3 2-B]1,2,4-Triazoles"Farmacia (Bucharest), vol. 47 (23), pp. 13-23 & Chemical Abstracts, Abstr. No. 131:348947, 1999.
Daniel Zahari et al., "Relations structure chimique-activite biologique dans la serie de quelques 2-aryl-5-r-thiazolo (3,2b) 1, 2,4-triazoles a activite antimicrobienne", Farmacia (Bucharest), vol. 47(2), pp. 51-60 & Chemical Abstracts, Abstr. No. 132:93254, 1999.

Primary Examiner—James O. Wilson
Assistant Examiner—Susanna Moore
(74) Attorney, Agent, or Firm—Hoxie & Associates LLC

(57)    ABSTRACT

The invention relates to isothiourea derivatives of formula I:

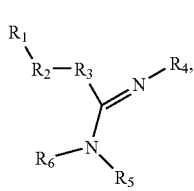

wherein $R_1$ is a residue of one of the following structures:

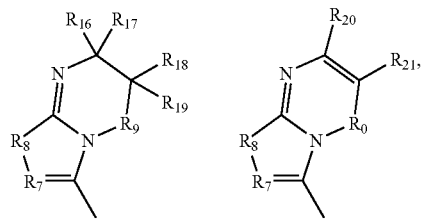

where the variables are as defined in the claims of the invention, as well as processes for production of these compounds.

7 Claims, No Drawings

ISOTHIOUREA DERIVATIVES OF IMADAZO[2,1-B]THIAZOLES AND 5,6-DIHYDRO DERIVATIVES THEREOF USEFUL AS CXCR4 CHEMOKINE RECEPTOR INHIBITORS

The present invention relates to isothiourea derivatives, processes for their production, their uses and pharmaceutical compositions containing them.

More particularly, the present invention provides a compound of formula I

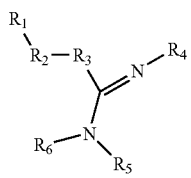

wherein $R_1$ is a residue of formula (a), (b) or (c)

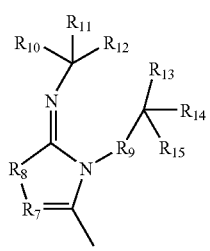

(a)

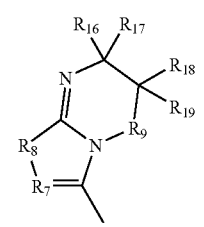

(b)

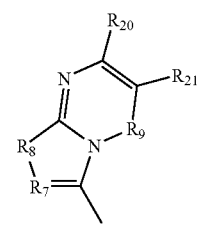

(c)

$R_2$ is —$(CR_{22}R_{23})_{1-3}$— or —C(O)—;

each of $R_3$ and $R_8$ independently is S; O; or $NR_{24}$;

each of $R_4$ and $R_5$ independently is optionally $R_{25}$-substituted $C_3$-$C_{12}$ cycloalkyl, $C_1$-$C_{12}$ alkyl or saturated $C_{8-12}$ polycyclic residue; or optionally $R_{26}$- and/or $R_{27}$-substituted aryl, aryl$C_{1-4}$alkyl or heteroaryl; wherein up to 4 carbon atoms of $R_4$ and/or $R_5$ are optionally substituted by S, O or $NR_{24}$;

$R_6$ is H; $C_1$-$C_6$ alkyl; $C_3$-$C_6$ cycloalkyl; or optionally $R_{26}$- and/or $R_{27}$-substituted aryl, aryl$C_{1-4}$alkyl or heteroaryl;

$R_7$ is $CR_{28}$ or N;

$R_9$ is a direct bond; —$(CR_{22}R_{23})_{1-2}$—; or $NR_{24}$;

each of $R_{10-23}$ and $R_{28}$ independently is H; F; Cl; Br; $C_1$-$C_6$ alkyl; $C_2$-$C_6$ alkoxyalkyl; $C_1$-$C_6$ halogenoalkyl; $C_3$-$C_6$ cycloalkyl; optionally $R_{26}$- and/or $R_{27}$-substituted aryl or heteroaryl; $CONR_{29}R_{30}$; $COOR_{29}$; CN; $NO_2$; or $OR_{31}$; or two of $R_{10-19}$ which are attached to the same carbon atom, together with the carbon atom to which they are attached, form a 3-7 membered nonaromatic ring optionally containing up to two heteroatoms selected independently from N, O and S; or $R_{17}$ and $R_{18}$, together with the C atoms to which they are attached, form a 4-7 membered nonaromatic ring optionally containing up to two heteroatoms selected independently from N, O and S; or $R_{20}$ and $R_{21}$, together with the carbon atoms to which they are attached, form an optionally $R_{26}$- and/or $R_{27}$-substituted aryl or heteroaryl;

each of $R_{24}$, $R_{29}$ and $R_{30}$ independently is H; $C_1$-$C_6$ alkyl; $C_2$-$C_6$ alkoxyalkyl; $C_1$-$C_6$ halogenoalkyl; $C_3$-$C_7$ cycloalkyl; or optionally $R_{26}$- and/or $R_{27}$-substituted aryl, aryl$C_{1-4}$alkyl or heteroaryl;

$R_{25}$ represents 1 to 4 substituents each independently having one of the significances given for $R_{10-23}$ above;

$R_{26}$ represents 1 to 4 substituents each independently selected from $C_1$-$C_6$ alkyl; $C_1$-$C_6$ hydroxyalkyl; $C_2$-$C_6$ alkoxyalkyl; $C_1$-$C_6$ halogenoalkyl; $C_3$-$C_6$ cycloalkyl; $C_2$-$C_6$ alkenyl; $C_3$-$C_6$ cycloalkenyl; $C_2$-$C_6$ alkynyl; aryl; heteroaryl; heteroaryl N-oxide; F; Cl; Br; I; OH; $OR_4$; $CONH_2$; $CONHR_4$; $CONR_4R_4$; $OC(O)R_4$; $OC(O)OR_4$; $OC(O)NHR_4$; $OC(O)NR_4R_4$; $OSO_2R_4$; COOH; $COOR_4$; $CF_3$; $CHF_2$; $CH_2F$; CN; $NO_2$; $NH_2$; $NHR_4$; $NR_4R_4$; $NHC(O)R_4$; $NR_4C(O)R_4$; $NHC(O)NHR_4$; $NHC(O)NH_2$; $NR_4C(O)NHR_4$; $NR_4C(O)NR_4R_4$; $NHC(O)OR_4$; $NR_4C(O)OR_4$; $NHSO_2R_4$; $N(SO_2R_4)_2$; $NR_4SO_2R_4$; $SR_4$; $S(O)R_4$; $SO_2R_4$; $Si(CH_3)_3$ and $B(OC(CH_3)_2)_2$;

$R_{27}$ represents two adjacent substituents which form an annulated 4-7 membered nonaromatic ring optionally containing up to two heteroatoms selected independently from N, O and S;

$R_{31}$ is $C_1$-$C_6$ alkyl; $C_3$-$C_7$ cycloalkyl; optionally $R_{26}$- and/or $R_{27}$-substituted aryl, aryl$C_{1-4}$alkyl or heteroaryl; or $CF_3$.

Any alkyl, alkenyl or alkynyl may be linear or branched. Halogeno is F, Cl, Br or I.

By aryl is meant phenyl or naphthyl.

The polycyclic residue may be for example optionally $R_{25}$-substituted adamantyl, bicyclo[3,2.1]octyl or

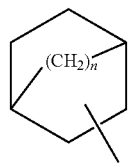

wherein n is 1 or 2.

By heteroaryl is meant an aromatic ring system comprising mono-, bi- or tricyclic systems which contains up to 4 heteroatoms independently selected from N, O and S. Examples of heteroaryl include e.g. pyridyl, indolyl, benzothiazolyl, thiazolyl, imidazolyl, benzimidazolyl. Examples of 3 to 7 membered nonaromatic rings containing 1 or 2 heteroatoms include e.g. morpholinyl, piperazinyl, piperidyl.

The compounds of formula I may exist in form of several interconverting tautomers and E/Z isomers, e.g.

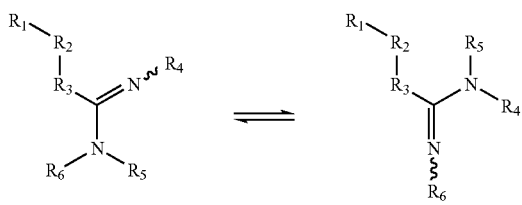

They may exist in free form or in salt form, e.g. addition salts with e.g. organic or inorganic acids, for example, hydrochloric acid, acetic acid. When the compounds of formula I have one or more asymmetric centers in the molecule, the present invention is to be understood as embracing the various optical isomers, as well as racemates, diastereoisomers and mixtures thereof.

In the compounds of formula 1, the following significances are preferred individually or in any sub-combination:

1. (a) Each of $R_{10-23}$ and $R_{28}$ independently is H; or $C_1$-$C_6$ alkyl;

(b) two of $R_{10-19}$ which are attached to the same carbon atom, together with the carbon atom to which they are attached, form a 3-6 membered nonaromatic ring optionally containing up to two heteroatoms selected independently from N, O and S; or (c) $R_{17}$ and $R_{18}$, together with the C atoms to which they attached, form a 4-7 membered nonaromatic ring optionally containing up to two heteroatoms selected independently from N, O and S; or 2. $R_9$ is a direct bond; or —$CR_{22}R_{23}$—;

3. each of $R_{24}$, $R_{29}$ and $R_{30}$ independently is H; $C_1$-$C_6$ alkyl; or $C_3$-$C_7$ cycloalkyl;

4. $R_7$ is $CR_{28}$;

5. $R_2$ is —$CR_{22}R_{23}$—;

6. each of $R_4$ and $R_5$ independently is optionally $R_{25}$-substituted $C_5$-$C_9$ cycloalkyl or $C_6$-$C_{12}$alkyl; or adamantyl; wherein optionally up to 4 carbon atoms of $R_4$ and/or $R_5$ are substituted by S, O or $NR_{24}$;

7. $R_6$ is H; or $C_1$-$C_6$ alkyl;

8. each of $R_3$ and $R_8$ independently is S;

9. aryl$C_{1-4}$alkyl is benzyl;

The invention also covers a process for preparing a compound of formula I comprising reacting a compound of formula II

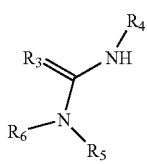

with a compound of formula III

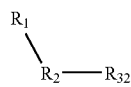

wherein $R_{1-6}$ are as defined above and $R_{32}$ is a leaving group;

and optionally converting a resultant compound of formula I obtained in free form to a salt form or vice versa.

Preferably $R_{32}$ is halogeno, more preferably chloro.

The compounds of formula III are known or may be prepared by reacting a compound of formula IV (a), (b) or (c)

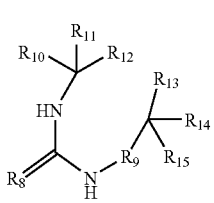

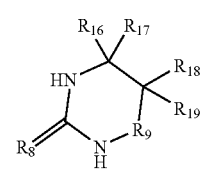

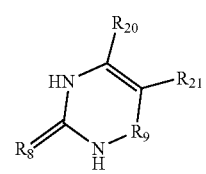

wherein $R_{8-21}$ are as defined above, with 1,3-dichloro-acetone, and recovering the compound of formula III in free or salt form.

The compounds of formulae II and IV are known and can be prepared according to procedures well established in the art.

The following examples illustrate the invention without any limitation.

EXAMPLE 1

1,3-dicyclohexyl-2-(5,6-dihydro-imidazo[2,1-b]thiazol-3-ylmethyl)-isothiourea

A mixture of N,N'-dicyclohexyl thiourea (0.21 g, 1.0 mmol), 3-chloromethyl-5,6-dihydro-imidazo[2,1-b]thiazole (0.72 g, 3.0 mmol) and acetonitrile (10 ml) is refluxed for 4 h. The precipitate is filtered off and crystallized from methanol/ether to give the dihydrochloride of 1,3-dicyclohexyl-2-(5,6-dihydro-imidazo[2,1-b]thiazol-3-ylmethyl)-isothiourea. MS/ESI 379 [M+H$^+$]

EXAMPLE 2

1,3-dicyclohexyl-2-(3-methyl-2-methylimino-2,3-dihydro-thiazol-4-ylmethyl)-isothiourea 1,3-dicyclohexyl-2-(3-methyl-2-methylimino-2,3-dihydro-thiazol-4-ylmethyl)-isothiourea is prepared from 4-chloromethyl-3-methyl-3H-thiazol-2-ylidene-methyl-amine using a procedure analogous to that described in example 1, except that the latter compound is used in place of 3-chloromethyl-5,6-dihydro-imidazo[2,1-b]thiazole. MS/ESI 381 [M+H$^+$].

(4-chloromethyl-3-methyl-3H-thiazol-2-ylidene)-methyl-amine used as starting material is prepared according to the following procedure:

A mixture of N,N'-dimethyl thiourea (1.04 g, 10.0 mmol), 1,3-dichloro acetone (1.27 g, 10.0 mmol) and n-butanol (25 ml) is heated at 140° C. for 1 h. The solvent is removed and the residue crystallized from methanol/ether to give the hydrochloride of (4-chloromethyl-3-methyl-3H-thiazol-2-ylidene)-methyl-amine. MS/ESI 177 [M+H$^+$].

EXAMPLE 3

1,3-dicyclohexyl-2-(6,6-dimethyl-5,6-dihydro-imidazo[2,1-b]thiazol-3-ylmethyl)-isothiourea 1,3-dicyclohexyl-2-(6,6-dimethyl-5,6-dihydro-imidazo[2,1-b]thiazol-3-ylmethyl)-isothiourea is prepared from 3-chloromethyl-6,6-dimethyl-5,6-dihydro-imidazo[2,1-b]thiazole using a procedure analogous to that described in example 1, except that the latter compound is used in place of 3-chloromethyl-5,6-dihydro-imidazo[2,1-b]thiazole. MS/ESI 407 [M+H$^+$].

3-Chloromethyl-6,6-dimethyl-5,6-dihydro-imidazo[2,1-b]thiazole used as starting material is prepared according to the following procedure:

A mixture of 4,4-dimethyl-imidazolidine-2-thione (1.0 g, 7.5 mmol), 1,3-dichloro acetone (1.00 g, 7.5 mmol) and acetonitrile (15 ml) is refluxed for 2 h. The colorless precipitate is filtered off, dried, suspended in 1-methoxy-2-(2-methoxy-ethoxy)-ethane and, subsequently, heated at 140° C. for 2 h. The precipitate is filtered of and washed with ether to give the hydrochloride of 3-chloromethyl-6,6-dimethyl-5,6-dihydro-imidazo[2,1-b]thiazole. MS/ESI 203 [M+H$^+$].

The following examples of formula V

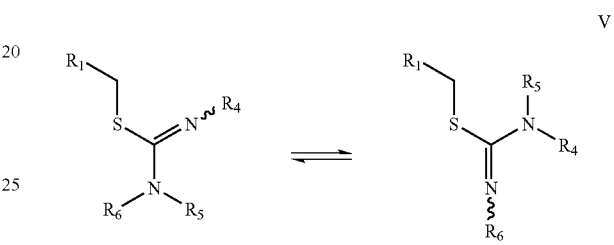

are prepared applying similar procedures.

| Example | R$_1$ | R$_4$ | R$_5$ | R$_6$ | M$^+$ |
|---|---|---|---|---|---|
| 4 | benzimidazo-thiazole | cyclohexyl | H | cyclohexyl | 427 |
| 5 | 6,7-dihydro-5H-imidazo[2,1-b]thiazole | cyclohexyl | H | cyclohexyl | 393 |
| 6 | 2,3-dihydro-imidazo[2,1-b]thiazole | cyclohexyl | Me | cyclohexyl | 393 |

-continued

| Example | R₁ | R₄ | R₅ | R₆ | M⁺ |
|---|---|---|---|---|---|
| 7 | imidazo-thiazoline | Me | H | Me | 243 |
| 8 | imidazo-thiazoline | isopropyl | H | isopropyl | 299 |
| 9 | imidazo-thiazoline | cyclopentyl | H | cyclopentyl | 351 |
| 10 | imidazo-thiazoline | cycloheptyl | H | cycloheptyl | 407 |
| 11 | imidazo-thiazoline | cyclooctyl | H | cyclooctyl | 435 |
| 12 | imidazo-thiazoline | H | H | cyclohexyl | 297 |
| 13 | imidazo-thiazoline | phenyl | H | cyclohexyl | 373 |
| 14 | imidazo-thiazoline | benzyl | H | cyclohexyl | 387 |

-continued
| Example | R$_1$ | R$_4$ | R$_5$ | R$_6$ | M$^+$ |
|---|---|---|---|---|---|
| 15 | 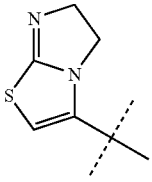 | 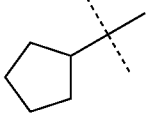 | H | 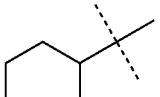 | 365 |
| 16 | 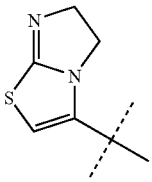 | 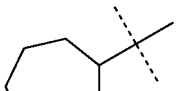 | H | 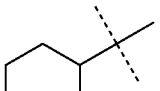 | 393 |
| 17 | 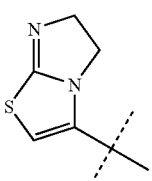 | 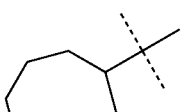 | H | 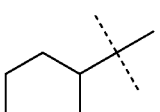 | 407 |
| 18 | 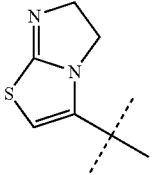 | 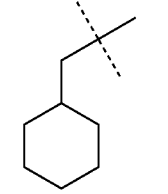 | H | 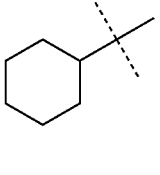 | 393 |
| 19 | 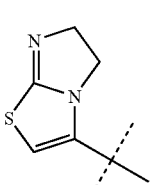 | 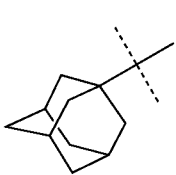 | H | 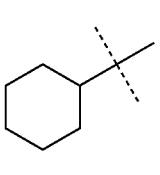 | 431 |
| 20 | 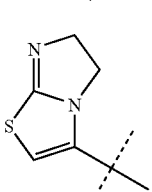 | 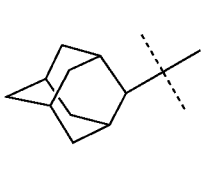 | H | 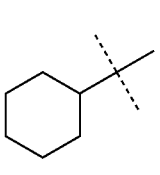 | 431 |
| 21 | 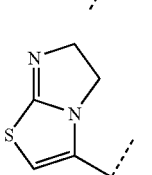 | 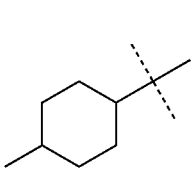 | H | 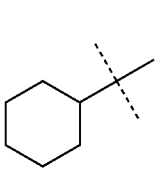 | 393 |
| 22 | 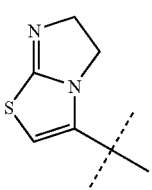 | n-hexyl | H | 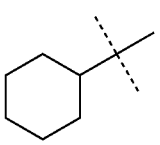 | 381 |

-continued

| Example | R₁ | R₄ | R₅ | R₆ | M⁺ |
|---|---|---|---|---|---|
| 23 | (imidazothiazole) | (tert-butylcyclohexyl) | H | (cyclohexyl) | 435 |
| 24 | (dimethyl imidazothiazole) | (cycloheptyl) | H | (cycloheptyl) | 435 |

The compounds of formula I in free form or in pharmaceutically acceptable salt form exhibit valuable pharmacological properties, e.g. as CXCR4 antagonists, e.g. as indicated in in vitro tests and therefore indicated for therapy. CXCR4 is a chemokine receptor G protein coupled receptor (GPCR) that is expressed in a variety of normal tissues, including monocytes. SDF-1 (CXCL12) is the cognate ligand of this receptor, and is known to act as a chemoattractant that drives chemotaxis of cells expressing CXCR4.

a) CXCR4 Membrane Binding Assay

Membranes are prepared from the T lymphoblast cell line CEM which endogenously expresses CXCR4. As radioligand 125-I labeled SDF-1α is used. Membranes, radioligand and a compound of formula I are incubated and the amount of bound radioligand determined. The data are reported as $IC_{50}$, i.e. the concentration of compound required to achieve 50% inhibition of [I-125]SDF-1α binding. In this assay compounds of formula I have an $IC_{50}$ of <50 µM.

b) CXCR4 Functional Assay—$Ca^{2+}$ Mobilization

SDF-1 induced $Ca^{2+}$ mobilization from intracellular stores is measured in CEM cells loaded with the $Ca^{2+}$-sensing fluorochrome Fluo-4. Fluo-4 loaded cells are incubated with compounds of formula I and then the SDF-1 induced increase in fluorescence is recorded in a fluorescence image plate reader. Inhibitory effects of compounds are expressed as $IC_{50}$ values, representing the concentration of compound which reduces the SDF-1 response by 50%. In this assay compounds of formula I have $IC_{50}$ values of <50 µM.

c) CXCR4 Functional Assay—Chemotaxis

Cell migration (chemotaxis) stimulated by SDF-1 is assessed in Transwell tissue culture inserts with porous polycarbonate membranes. Target cells (eg. Jurkat T cells, CEM cells or lymphocytes) are added to the upper compartment and the chemokine SDF-1 to the lower compartment. Compounds of formula I are added to both compartments at the same concentration. Compounds of formula I inhibit SDF-1 induced chemotaxis with $IC_{50}$ values<50 µM.

The compounds of formula I are, therefore, useful in the prevention and/or treatment of diseases or disorders mediated by interactions between chemokine receptors, e.g. CXCR4, and their ligands, e.g. in transplantation, such as acute or chronic rejection of organ, tissue or cell allo- or xenografts or delayed graft function, autoimmune diseases, e.g. rheumatoid arthritis, systemic lupus erythematosus, Hashimoto's thyroidis, multiple sclerosis, myasthenia gravis, diabetes type I or II and the disorders associated therewith, vasculitis, pernicious anemia, Sjoegren syndrome, uveitis, psoriasis, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock and others, infectious diseases, e.g. toxic shock (e.g. superantigen induced), septic shock, adult respiratory distress syndrome or viral infections, e.g. binding or entry of the HIV virus into cells expressing CXCR4, or progression of AIDS. By transplantation is meant allo- or xeno grafts of e.g. cells, tissues or solid organs, for example pancreatic islets, stem cells, bone marrow, corneal tissue, neuronal tissue, heart, lung, combined heart-lung, kidney, liver, bowel, pancreas, trachea or oesophagus. Chronic rejection is also named graft vessel disease.

CXCR4 signaling is implicated in the progression, invasion, or metastasis of tumors, e.g. solid tumors. Stromal or epithelial cells associated with primary tumors have been observed to often express SDF-1. CXCR4/SDF-1 interactions are involved in establishment, growth, angiogenesis, or localized invasion of the tumor at the primary site, e.g. blood vessel development, or promotion of entry of tumor cells into the blood or lymphatic circulation via SDF-1 expression by cells associated with blood vessels, e.g. in the early steps of metastasis.

In addition, SDF-1 expression by bone marrow cells promotes recruitment, adherence or proliferation of tumor cells expressing CXCR4 in bone. SDF-1 expression at other sites or tissues plays a similar role in metastasis or establishment of tumors at those sites. Multiple myeloma is an example of a cancer in which recruitment of cells to the bone marrow plays a critical homing, environmental and proliferative role in establishment and progression.

Compounds of the invention are therefore also useful in the prevention or treatment of proliferative diseases, especially malignant proliferative or neoplastic diseases, e.g. tumors, for example brain and other central nervous system tumors (eg. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

Where hereinbefore and subsequently a tumor, a tumor disease, a carcinoma or a cancer is mentioned, also metastasis in the original organ or tissue and/or in any other location are implied alternatively or in addition, whatever the location or locations of the tumor and/or metastasis. The compounds of formula I are particularly indicated for treating tumor invasiveness or symptoms associated with such tumor growth, preventing metastatic spread of tumours or for preventing or inhibiting growth of micrometastasis in a subject in need thereof, especially for treating or preventing metastatic spread of tumors to bone, e.g. to bone marrow. In one embodiment, the compounds of formula I are indicated for preventing or treating metastasis, tumor invasiveness or tumor growth mediated by CXCR4 receptors and/or SDF-1 expression.

In a further embodiment, the compounds of formula I are indicated for inhibiting or controlling deregulated angiogenesis, e.g. angiogenesis mediated by CXCR4 and/or SDF-1, in a subject in need thereof.

For the above uses the required dosage will of course vary depending on the mode of administration, the particular condition to be treated and the effect desired. In general, satisfactory results are indicated to be obtained systemically at daily dosages of from about 0.01 to 10 mg/kg per body weight. An indicated daily dosage in the larger mammal, e.g. humans, is in the range from about 0.5 mg to about 1000 mg, conveniently administered, for example, in divided doses up to four times a day or in retard form. Suitable unit dosage forms for oral administration comprise from 0.1 to 500 mg, e.g. from ca. 0.5 to 4 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by interactions between chemokine receptors, e.g. CXCR4 receptors, and their ligands, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or inflammatory or autoimmune diseases, e.g. as indicated above, in a subject in need of such treatment, which method comprises administering to said subject an effective amount of a compound of formula I or a pharmaceutically acceptable salt thereof;

1.3 A method for preventing or treating a proliferative disease, e.g. as indicated above, in a subject in need of such treatment, which method comprises administering to said subject an effective amount of a compound of formula I or a pharmaceutically acceptable salt thereof;

1.4 A method for treating tumor progression, invasiveness or symptoms associated with such tumor growth, preventing metastatic spread of tumours or for preventing or inhibiting growth of micrometastases, or for preventing tumor associated angiogenesis, e.g. as indicated above, in a subject in need of such treatment, which method comprises administering to said subject an effective amount of a compound of formula I or a pharmaceutically acceptable salt thereof;

1.5 A method for preventing or combating infectious diseases, e.g. viral infection, in particular for preventing or combating the binding or entry of a virus into cells expressing chemokine receptor, e.g. the binding or entry of the HIV virus, such as HIV-1 or HIV-2, into cells expressing CXCR4, or progression of AIDS.

2. A compound of formula I or a pharmaceutically acceptable salt thereof for use as a pharmaceutical, e.g. in any of the methods as indicated under 1.1 to 1.4 above.
3. A pharmaceutical composition, e.g. for use in any of the methods as in 1.1 to 1.4 above comprising a compound of formula I or a pharmaceutically acceptable salt thereof in association with a pharmaceutically acceptable diluent or carrier therefor.
4. A compound of formula I or a pharmaceutically acceptable salt thereof for use in the preparation of a pharmaceutical composition for use in any of the method as in to 1.4 above.

The compounds of formula I may be administered as the sole active ingredient or in conjunction with, e.g. as an adjuvant to, other drugs e.g. in immunosuppressive or immunomodulating regimens or other anti-inflammatory agents, e.g. for the treatment or prevention of allo- or xenograft acute or chronic rejection or inflammatory or autoimmune disorders, a chemotherapeutic agent or an anti-infective agent, e.g. an anti-viral agent such as e.g. an anti-retroviral agent or an antibiotic. For example, the compounds of formula I may be used in combination with a calcineurin inhibitor, e.g. cyclosporin A or FK 506; an mTOR inhibitor, e.g. rapamycin, 40-O-(2-hydroxyethyl)-rapamycin, CCI779, ABT578, AP23573, AP23464, AP23675, AP23841 or TAFA-93; an ascomycin having immunosuppressive properties, e.g. ABT-281, ASM981, etc.; corticosteroids; cyclophosphamide; azathioprine; methotrexate; leflunomide; mizoribine; mycophenolic acid; mycophenolate mofetil; 15-deoxyspergualine or an immunosuppressive homologue, analogue or derivative thereof; a sphingosine-1-phosphate receptor agonist, e.g. FTY720; monoclonal antibodies to leukocyte receptors, e.g., MHC, CD2, CD3, CD4, CD7, CD8, CD11a/CD18, CD25, CD27, CD28, CD40. CD45, CD58, CD80, CD86, CD137, ICOS, CD150 (SLAM), OX40, 4-1BB or to their ligands, e.g. CD154, or antagonists thereof; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4lg (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antichemokine antibodies or antichemokine receptor antibodies or low molecular weight chemokine receptor antagonists, e.g. anti MCP-1 antibodies.

The term "anti-viral agent" as used herein includes, but is not limited to, anti-retroviral agent; antibody against virus; e.g. anti-HIV antibody; inhibitor of reverse transcriptase; e.g. inhibitor of HIV reverse transcriptase, especially nucleoside analogues, such as Retrovir® (3'-azido-3'-deoxypyrimidine, Zidovudine) and 3'-azido-3'-deoxythymidine (AZT) from GlaxoSmithKline, HIVID® (2',3'-dideoxycytidine, Zalcitabine) from Hoffmann-LaRoche, Videx® or VidexEC® (2',3'-dideoxyinosine, Didanosine) from Bristol-Myers-Squibb, Epivir® (Lamivudine) from GlaxoSmithKline, Zerit® (stavudine) from Bristol Myers-Squibb, Viread® (tenofovir DF) from Gilead, ziagen® (abacavir) from GlaxoSmithKline, Emtriva® (Emtricitabine, FTC) from Gilead Sciences; or non-nucleoside analogues, such as e.g. rescriptor® (delavirdine) from Pfizer, Sustiva® (Efavirenz) from Bristol Meyer Squibb, viramune® (nevirapine) from Boehringer-Ingelheim; 11-cyclopropyl-5,11-dihydro-4-methyl-(6H)-dipyrido [3,2-b;2',3'-e]-[1,4]diazepin-6-one, trisodium phosphonoformate, ammonium-21-tungstenato-9-antimonate, 1-β-D-ribofuranoxyl-1,2,4-triazole-3-carboxamide; inhibitor of viral or retroviral protease, e.g. inhibitor of viral aspartate protease, e.g. inhibitor of HIV protease, such as aganerase® (amprenavir) from GlaxoSmithKline, reyataz® (atazanavir) from Bristol-Myers Squibb, lexiva® (fosamprenavir) from GSK, Crixivan® ((Indinavir) from Merck & Co.; viracept® (nelfinavir) from Agouron, norvir® (Ritonavir) from Abbott; fortovase® and Invirase® (saquinavir) from Hoffmann-LaRoche; and other compounds such as lasinavir (5(S)-(tert-butoxycarbonylamino)-4(S)-hydroxy-6-phenyl-2(R)(2,3,4-trimethoxyphenylmethyl)-hexanoyl-(L)-valyl-N-(2-methoxy-ethyl)-amide), Adriamycin, KVX-478 from GlaxoWellcome; VX-478 from Vertex; 141 W94 from Kissei Pharmaceuticals; AG-1343 from Agouron; KNI-272 from Nippon Mining; U-96988 from Upjohn; BILA-2011BS (Palinavir) from Boehringer-Ingelheim; compounds preventing virus penetration, such as e.g. polymannoacetate; fusion inhibitors, such as e.g. fuzeon® (enfuvirtide, T-20) from Hofffmann-LaRoche; or any combination thereof, such as Epzicom® (Abacavir and Lamivudine) from GlaxoKlineSmith, Trizivir® (Abacavir, Lamivudine and Zidovudine) from GlaxoKlineSmith, Truvada® (Emtricitabine and Tenofir DF) from Gilead Sciences, Combivir® (Lamivudine and Zidovudine) from GlaxoKlineSmith, kaletra® (lopinavir and ritonavir) from Abbott. The term "anti-viral agent" further includes agent which treats the opportunistic infectious which are caused by the immunosuppression resulting from viral infection, e.g. HIV infection.

The term "HIV" as used herein includes, but is not limited to, HIV-1 and HIV-2.

A compound of formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitro-camptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285; compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;

compounds which decreases the activity of the protein kinase C are especially those staurosporine derivatives disclosed in EP 0 296 110 (pharmaceutical preparation described in WO 00/48571) which compounds are protein kinase C inhibitors;

further specific compounds that decrease protein kinase activity and which may also be used in combination with the compounds of the present invention are Imatinib (Gleevec®/Glivec®), midostaurin, Iressa™ (ZD1839), PKI166, Vatalanib, ZD6474, GW2016, CHIR-200131, CEP-7055/CEP-5214, CP-547632 and KRN-633;

anti-angiogenic compounds having another mechanism of action than decreasing the protein kinase activity include, but are not limited to e.g. thalidomide (THALOMID), celecoxib (Celebrex), SU5416 and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™.

Abarelix can be formulated, e.g. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having antiproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and midostaurin.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula I, can be prepared and administered as described in the art such as in the documents cited above.

Where the compounds of formula I are administered in conjunction with other immunosuppressive/immunomodulatory, anti-inflammatory, antiproliferative, anti-infective, anti-viral or chemotherapeutic therapy, dosages of the co-administered immunosuppressant, immunomodulatory, anti-inflammatory, antiproliferative, anti-infective, anti-viral or chemotherapeutic compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory, antiproliferative, antineoplatic anti-infective, anti-viral, antibiotic or chemotherapeutic drug, e.g. as indicated above.

6. A pharmaceutical combination, e.g. a kit, comprising a) a first agent which is a CXCR4 antagonist, e.g. a compound of formula I as disclosed herein, in free form or in pharmaceutically acceptable salt form, and b) at least one co-agent, e.g. an immunosuppressant, immunomodulatory, anti-inflammatory, antiproliferative, anti-infective or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, e.g. viral agent, are both administered to a patient simultaneously in the form of a single entity or dosage. The term "non-fixed combination" means that the active ingredients, e.g. a compound of formula I and a co-agent, e.g. viral agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:
1. A compound of formula I:

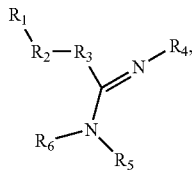

wherein
$R_1$ is a residue of formula (b) or (c)

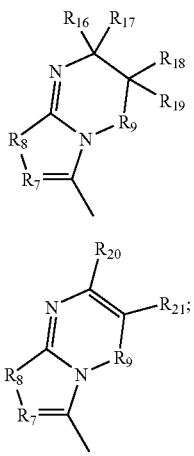

$R_2$ is —$(CR_{22}R_{23})_{1-3}$— or —C(O)—;
each of $R_3$ and $R_8$ is S;
each of $R_4$ and $R_5$, independently, is optionally $R_{25}$-substituted $C_3$-$C_{12}$-cycloalkyl, $C_1$-$C_{12}$-alkyl or saturated $C_{8-12}$-polycyclic residue; or optionally $R_{26}$- and/or $R_{27}$-substituted aryl, aryl$C_{1-4}$-alkyl or heteroaryl;
$R_6$ is H; $C_1$-$C_6$-alkyl; $C_3$-$C_6$-cycloalkyl; or optionally $R_{26}$- and/or $R_{27}$-substituted aryl, aryl$C_{1-4}$-alkyl or heteroaryl;
$R_7$ is $CR_{28}$;
$R_9$ is a direct bond;
each of $R_{16}$, $R_{17}$, $R_{18}$, $R_{19}$, $R_{20}$, $R_{21}$, $R_{22}$, $R_{23}$ and $R_{28}$, independently, is H; F; Cl;
Br; $C_1$-$C_6$-alkyl; $C_2$-$C_6$-alkoxyalkyl; $C_1$-$C_6$-halogenoalkyl; $C_3$-$C_6$-cycloalkyl;
optionally $R_{26}$- and/or $R_{27}$-substituted aryl or heteroaryl; CONR$_{29}$R$_{30}$; COOR$_{29}$;
CN; NO$_2$; or OR$_{31}$;
each of $R_{29}$ and $R_{30}$, independently, is H; $C_1$-$C_6$-alkyl; $C_2$-$C_6$-alkoxyalkyl; $C_1$-$C_6$-halogenoalkyl; $C_3$-$C_7$-cycloalkyl; or optionally $R_{26}$- and/or $R_{27}$-substituted aryl, aryl$C_{1-4}$-alkyl or heteroaryl;
$R_{25}$ represents 1-to-4 substituents each, independently, H; F; Cl; Br; $C_1$-$C_6$-alkyl;
$C_2$-$C_6$-alkoxyalkyl; $C_1$-$C_6$-halogenoalkyl; $C_3$-$C_6$-cycloalkyl; optionally $R_{26}$- and/or
$R_{27}$-substituted aryl or heteroaryl; CONR$_{29}$R$_{30}$; COOR$_{29}$; CN; NO$_2$; or OR$_{31}$;
$R_{26}$ represents 1-to-4 substituents each, independently, selected from $C_1$-$C_6$-alkyl; $C_1$-$C_6$-hydroxyalkyl; $C_2$-$C_6$-alkoxyalkyl; $C_1$-$C_6$-halogenoalkyl; $C_3$-$C_6$-cycloalkyl;
$C_2$-$C_6$-alkenyl; $C_3$-$C_6$-cycloalkenyl; $C_2$-$C_6$-alkynyl; aryl; heteroaryl;
heteroaryl N-oxide; F; Cl; Br; I; OH; OR$_4$; CONH$_2$; CONHR$_4$; CONR$_4$R$_4$;
OC(O)R$_4$; OC(O)OR$_4$; OC(O)NHR$_4$; OC(O)NR$_4$R$_4$; OSO$_2$R$_4$; COOH; COOR$_4$;
CF$_3$; CHF$_2$; CH$_2$F; CN; NO$_2$; NH$_2$; NHR$_4$; NR$_4$R$_4$; NHC(O)R$_4$; NR$_4$C(O)R$_4$;
NHC(O)NHR$_4$; NHC(O)NH$_2$; NR$_4$C(O)NHR$_4$; NR$_4$C(O)NR$_4$R$_4$; NHC(O)OR$_4$;
NR$_4$C(O)OR$_4$; NHSO$_2$R$_4$; N(SO$_2$R$_4$)$_2$; NR$_4$SO$_2$R$_4$; SR$_4$; S(O)R$_4$; SO$_2$R$_4$; Si(CH$_3$)$_3$ and B(OC(CH$_3$)$_2$)$_2$;
$R_{27}$ represents two adjacent substituents which form an annulated 4-7-membered nonaromatic ring optionally containing up to two heteroatoms selected, independently, from N, O and S;
$R_{31}$ is $C_1$-$C_6$-alkyl; $C_3$-$C_7$-cycloalkyl; optionally $R_{26}$- and/or $R_{27}$-substituted aryl, aryl$C_{1-4}$-alkyl or heteroaryl; or CF$_3$;
or a pharmaceutically-acceptable salt thereof.

2. A compound according to claim 1 which is selected from 1,3-dicyclohexyl-2-(5,6-dihydro-imidazo[2,1-b]thiazol-3-ylmethyl)-isothiourea, 1-cyclohexyl-3-cyclopentyl-2-(5,6-dihydro-imidazo[2,1-b]thiazol-3-ylmethyl)-isothiourea, 1-cycloheptyl-3-cyclohexyl-2-(5,6-dihydro-imidazo[2,1-b]thiazol-3-ylmethyl)-isothiourea, 1,3-dicycloheptyl-2-(5,6-dihydroimidazo[2,1-b]thiazol-3-ylmethyl)-isothiourea, 1-cyclohexyl-3-cyclooctyl-2-(5,6-dihydroimidazo[2,1-b]thiazol-3-ylmethyl)-isothiourea, 1,3-dicyclohexyl-2-(6,6-dimethyl-5,6-dihydroimidazo[2,1-b]thiazol-3-ylmethyl)-isothiourea, 1,3-dicyclooctyl-2-(5,6-dihydroimidazo[2,1b]thiazol-3-ylmethyl)-isothiourea and 1,3-dicycloheptyl-2-(6,6-dimethyl-5,6-dihydroimidazo[2,1-b]thiazol-3-ylmethyl)-isothiourea.

3. A pharmaceutical composition comprising a compound according to claim 1 in free form or in a pharmaceutically-acceptable salt form and a pharmaceutically-acceptable diluent or carrier thereof.

4. A process for preparing a compound of formula I according to claim 1 comprising reacting a compound of formula II

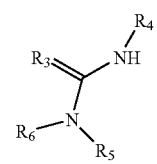

with a compound of formula III

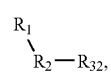

wherein $R_1$ to $R_6$ are as defined in claim 1, and $R_{32}$ is a leaving group; and
optionally converting the resultant compound of formula I obtained in free form to a salt form or vice versa.

5. A pharmaceutical combination comprising a compound according to claim 1 in free form or in a pharmaceutically-acceptable salt form and a further agent selected from immunosuppressive, immunomodulating, anti-inflammatory, antiproliferative, antineoplastic, chemotherapeutic, anti-infective, anti-viral, and antibiotic agents, and agents for the treatment of acute myeloid leukemia.

6. The pharmaceutical combination according to claim 5 comprising an antiretroviral agent.

7. The pharmaceutical combination according to claim 6, wherein the antiretroviral agent is an anti-HIV agent.

* * * * *